United States Patent [19]

Jurewicz et al.

[11] 3,932,305

[45] Jan. 13, 1976

[54] V-P-ZR CATALYSTS AND METHOD OF PREPARATION THEREOF IN THE ABSENCE OF HYDROGEN HALIDE

[75] Inventors: Anthony T. Jurewicz; Lewis Brewster Young, both of Kendall Park, N.J.

[73] Assignee: Mobil Oil Corporation, New York, N.Y.

[22] Filed: Apr. 17, 1974

[21] Appl. No.: 461,668

[52] U.S. Cl............. 252/429 R; 252/428; 252/435; 252/437; 260/346.8 A
[51] Int. Cl.² .......................................... B01J 27/18
[58] Field of Search.. 260/346.8 A; 252/428, 429 R, 252/430, 435, 437

[56] References Cited
UNITED STATES PATENTS

| | | | |
|---|---|---|---|
| 2,773,921 | 12/1966 | Rylander et al. ............... | 252/435 X |
| 3,156,705 | 11/1964 | Kerr............................... | 252/437 X |
| 3,156,707 | 11/1964 | Kerr............................... | 252/437 X |
| 3,293,268 | 12/1966 | Bergman et al................. | 252/437 X |
| 3,684,741 | 8/1972 | Friedrichsen et al. .......... | 252/437 X |
| 3,832,359 | 8/1974 | Freerks et al................... | 252/437 X |

*Primary Examiner*—Patrick P. Garvin
*Attorney, Agent, or Firm*—Charles A. Huggett; Hastings S. Trigg

[57] ABSTRACT

V-P-Zr catalysts having high activity and selectivity and good physical strength for the oxidation of alkanes, cycloalkanes and mixtures rich in them to dicarboxylic acid anhydrides (e.g. maleic anhydride) are prepared by reacting an aqueous mixture of vanadium pentoxide and a hydroxy-or oxo- alkanoic acid or formaldehyde, a zirconium salt, and phosphoric acid.

5 Claims, No Drawings

V-P-ZR CATALYSTS AND METHOD OF PREPARATION THEREOF IN THE ABSENCE OF HYDROGEN HALIDE

CROSS-REFERENCE TO RELATED APPLICATIONS

This application is related to copending application Ser. No. 461,777 filed concurrently herewith, now U.S. Pat. No 3,888,886, which describes catalysts comprising complex reaction products of a vanadium oxy salt and phosphoric acid promoted with certain metals, and which is a continuation-in-part of Ser. No. 379,667, filed July 16, 1973 now abandoned, which is continuation-in-part of Ser. No. 261,030, filed June 8, 1972 now abandoned.

BACKGROUND OF THE INVENTION

1. Field of the Invention

This invention has to do with a method for preparing vanadium-phosphorus-zirconium catalysts with high activity and selectivity and good physical strength for the oxidation of alkanes, cycloalkanes and mixtures rich therein to dicarboxylic acid anhydrides, particularly butane to maleic anhydride.

2. Description of the Prior Art

Vanadium-phosphorus complex catalysts for the oxidation of butane to maleic anhydride, are described in U.S. Pat. No. 3,293,268. Such catalysts operate at temperatures greater than 500°C. In general, yields of maleic anhydride with such catalysts are relatively low and not commercially attractive or feasible.

More recently, catalysts comprising antimony, molybdenum and iron or vanadium, have been described for oxidizing $C_4$ and $C_5$ paraffin hydrocarbons to maleic anhydride. The catalysts are indicated to be useful at 300°–600°C.

Metal-promoted vanadium-phosphorus complex catalysts are described in U.S. Pat. No. 3,156,705. The metal promoters, identified as phosphorus stabilizers, are broadly disclosed to include transition metals and rare earth metals. The catalysts are taught for oxidizing an olefin (butene) to a dicarboxylic acid anhydride (maleic anhydride). There is no teaching that such catalysts are effective in the more difficult oxidation of saturated hydrocarbons (alkanes and cycloalkanes).

In application Ser. No. 261,030, filed June 8, 1972 now abandoned, there is described an improved process for oxidizing an alkane to a dicarboxylic acid anhydride in the presence of a catalyst comprising a complex reaction product of a vanadium oxysalt and phosphoric acid promoted with one or more of Cr, Fe, Hf, Zr, La and Ce. The atomic ratio of P/V is between about 0.5 and about 2, and the atomic ratio of promoter metal/V is between about 0.0025 and about 1, in such catalysts.

As an improvement over, and an extension of, the catalysts described in said application Ser. No. 461,777, now U.S. Pat. No. 3,888,886, the present invention is concerned with a particular method for making V/P/Zr catalysts and with the particular catalysts obtained with that method. In prior catalyst preparation methods using HCl, at least 5 moles or more of HCl were required per gram atom of vanadium. Such preparation method presents a high corrosivity problem requiring the use of expensive corrosion resistant equipment. It also increases the volume of material that must be handled. The method of this invention, however, does not involve the use of hydrogen halide (HCl) and eliminates problems associated with its use. When the vanadium source is a halogen-containing vanadium salt, the amount of by-product hydrogen halide encountered is relatively and comparatively small and involves a relatively negligible problem.

SUMMARY OF THE INVENTION

In accordance with the present invention, there is provided a method for preparing vanadium-phosphorus-zirconium composites which are catalytically active and selective for the oxidation of an alkane, cycloalkane or mixtures thereof to a dicarboxylic acid anhydride and which have high physical strength. The method comprises forming an aqueous mixture of vanadium compound, a hydroxy- or oxoalkanoic acid ($C_2$-$C_3$) or formaldehyde, adding a zirconium salt, and phosphoric acid or a compound which hydrolyzes to phosphoric acid to form a slurry, and drying the slurry.

The invention is also concerned with a process for oxidizing an alkane, cycloalkane or mixtures rich in them to a dicarboxylic acid anhydride by contacting the alkane with a molecular oxygen-containing gas under specified conditions in the presence of said composites.

DESCRIPTION OF SPECIFIC EMBODIMENTS

The catalysts produced by the method of this invention are effective in the oxidation of alkanes, cycloalkanes, and mixtures rich in alkanes and cycloalkanes to maleic anhydride in good yields and with good selectivity. These catalysts also have the high physical strength needed to be used in fluid bed reactors.

Although the catalyst components can be reacted using various orders of addition, it is preferred to prepare the catalyst in three steps or stages. First, an aqueous slurry of vanadium compound and a hydroxy- or oxo- alkanoic acid ($C_2$-$C_3$) or formaldehyde is refluxed at 100°–120°C. for between about 0.5 hour and about 5 hours. Then, a zirconium salt is added and refluxing is continued for another 0.5 hour to 5 hours. Finally, phosphoric acid or a compound hydrolyzable to phosphoric acid such as $P_2O_5$; is added and refluxing is continued (between about 0.5 hour and about 5 hours).

Vanadium compounds employable herein are $V_2O_5$, $VOCl_3$, $VO(NO_3)_3$, $NH_4VO_3$ and $VF_5$, of which $V_2O_5$ is particularly preferred. The zirconium salts are illustrated by $ZrOCl_2.4H_2O$, $ZrOCl_2.8H_2O$, $ZrO(OAc)_2.H_2O$, $ZrCl_4$, $Zr(OAc)_4$, $Na_2ZrCl_6$ and $ZrOBr_2.XH_2O$.

The reactant that is reacted with the vanadium compound in the production of the catalysts of this invention is a hydroxy- or oxo- alkanoic acid having 2–3 carbon atoms or formaldehyde. Non-limiting examples of such acids are glyoxylic acid, pyruvic acid, glycolic acid, and lactic acid. Glycolic acid and pyruvic acid are preferred.

The molar ratio of the hydroxy- or oxo-alkanoic acid or formaldehyde to vanadium compound will be between about 0.05 and about 1. The optimum ratio for each acid or formaldehyde can be readily determined by a minimum number of experiments, as those skilled in the art will appreciate. In the case of glycolic acid, optimum ratios appear to be 0.3–0.5 in order to obtain a catalyst with high selectivity and activity and good physical strength. The ratios for other reactants will vary within the aforementioned range.

The quantity of zirconium salt employed is from about 0.0025 to about 0.5 gram atom per gram atom of vanadium compound. Thus, the quantities of vanadium compound and zirconium salt are such that the atomic ratio of Zr/V of the final composite is between about 0.0025 and about 0.5.

The solution formed with the final step addition of phosphoric acid is refluxed, to form a slurry. The phosphorus/vanadium atomic ratio wiill be about 1.1–1.5/1. Accordingly, there will be used between about 1.1 gram atoms and about 1.5 gram atoms of phosphoric acid or compound hydrolyzable thereto per gram atom of vanadium compound. A P/V atomic ratio of about 1.1/1 is preferred.

Then, the slurry is concentrated and evaporated to substantially dry condition in trays or by spray drying. The dried material is ground to about 20–60 mesh (U.S. Sieve Series) for fixed bed operation. The ground material can be pelletized, for example, to 1/8 inch × 5/32 inch cylindrical pellets. Optionally, a binder such as stearic acid, can be added before pelletizing. Alternatively, the catalyst solution, before drying, can be used to impregnate a suitable carrier such as alumina, alundum, silica, silicon carbide, silica-alumina, zirconia, zirconium phosphate, and/or a zeolite, to produce a supported catalyst suitable for use in a fixed or fluidized bed reactor. As a further and preferred alternative, the dried, unsupported catalyst can be ground to produce a powdered catalyst (e.g., 60–200 mesh) for use in a fluidized bed reactor.

The catalyst can be conditioned in the reactor by passing a hydrocarbon-air mixture through the catalyst bed as at about 450°C., prior to running the oxidation reaction. Such conditioning is, however, not necessary to obtain catalyst efficiency. In practice, anhydride product can be obtained upon commencing the flow of oxidation feed through the reactor.

The charge stocks utilizable in the process using the catalyst of this invention are alkanes having between 4 and 10 carbon atoms, or mixtures of hydrocarbons rich in alkanes and cycloalkanes having between 4 and 10 carbon atoms. The alkanes can be normal alkanes or they can have branching. Typical alkanes are butane, pentane, isopentane, hexane, 3-methylpentane, heptane, octane, isooctane, and decane. The cycloalkanes utilizable can be methyl substituted and include cyclobutane, cyclopentane, methylcyclopentane, cyclohexane, methylcyclohexane, 1,4-dimethylcyclohexane, cycloheptane, and cyclooctane. Mixtures of hydrocarbons rich in alkanes and cycloalkanes having between 4 and 10 carbon atoms, i.e., containing about 70 weight percent or more alkanes and cycloalkanes, are well known in the art. Particularly suitable and readily available mixtures are naphthas obtained from paraffinic or naphthenic petroleum sources. Full boiling range naphthas (boiling within the range of about 35°–230°C.) can be used but it is preferred to use light naphtha cuts boiling within the range of about 35°–145°C. The naphthas usually contain about 5–15 percent benzene and alkylbenzenes. It has been found that benzene is oxidized to maleic anhydride in the process of this invention, whereas to some extent alkylbenzenes are oxidized to benzene carboxylic acids or phthalic anhydride. It will be understood that other mixtures can be used, such as a paraffinic raffinate from the glycol-water solvent extraction of reformates (Udex process).

Butane, because of its ready availability, is preferred. In the following discussion and exemplification, therefore, butane is used in most examples to demonstrate (but not to limit) the present process for producing maleic anhydride. It is contemplated that mixtures rich in butane can be used, such as a typical butane-butene (B—B) refinery stream.

The oxidation of n-butane (or other feed as aforedefined) to maleic anhydride is carried out using air or other molecular oxygen-containing gases, such as mixtures of carbon dioxide and oxygen or mixtures of nitrogen or steam with air or oxygen. Air is preferred. The oxidation reaction is carried out at temperatures of 300°–600°C., preferably 325°–550°C. The feed concentration is 0.5–6 volume percent butane in the oxygen-containing gas and preferably 1–5 volume percent. The contact time is generally varied between about 0.08–3 seconds, preferably about 0.16–1.6 seconds for fixed bed operation. Generally, contact times of up to about 30 seconds can be used in the case of fluidized bed operation. Thus, contact time, depending upon the type of operation, will be about 0.08–30 seconds. Although the reaction can be carried out at 0.5–20 atmospheres pressure (absolute), it is preferably carried out at about 1–5 atmospheres.

The reaction can be carried out in any suitable reactor for effecting vapor phase oxidation reactions. For example, a fixed catalyst bed can be employed. The reaction can be carried out, preferably, by using smaller catalyst particles in a fluidized reactor bed.

In the examples and tables, percent yield of "MA" indicates maleic anhydride yield expressed as weight of desired product based upon weight of (butane) feed (wt. percent) and was determined by titration.

Similarly, selectivity to maleic anhydride is represented by:

$$\frac{\text{moles of maleic anhydride product}}{\text{moles of hydrocarbon feed reacted}} \times 100.$$

Contact time is determined by:

$$\frac{\text{quiescent catalyst bed volume}}{\text{volumetric flow rate at reactor temperature and pressure.}}$$

The flow rates of air and butane were measured at room temperature and pressure.

The attrition index (A.I.) is a relative rating of the percent fines produced from the catalyst under test compared to the fines produced from a commercial vanadium sulfate (about 3 percent) on silica gel catalyst (Grace No. 906) used in a fluid process for oxidizing naphthalene to phthalic anhydride. The percent fines is determined in 1 inch I.D. copper tube fluid bed apparatus provided at the top with a disengaging section adapted to retain particles of 40 microns or greater in diameter and provided with a thimble to entrap smaller size particles, i.e., fines. In operation, a weighed sample (about 20 ml.) of catalyst is placed in the fluid bed apparatus and the thimble is tared. Air is passed upwardly through the bottom of the tube at a rate of 13 liters per minute. After one hour, the air flow is stopped and the tared thimble is weighed to determine the weight of fines. The percent of fines is calculated.

$$\% \text{ fines} = \frac{\text{g. of fines collected}}{\text{g. of catalyst charged}} \times 100$$

$$\text{Attrition Index (A.I.)} = \frac{\% \text{ fines from test catalyst}}{\% \text{ fines from commercial catalyst}}$$

EXAMPLE 1

A vanadium-phosphorus-zirconium catalyst having a V/P/Zr atomic ratio of 1/1.2/0.13 was prepared as follows: 129g. of $V_2O_5$ and 30 ml. of 70 percent aqueous glycolic acid (GA) solution (0.33 mole) was added to 500 ml. of $H_2O$. The mixture was refluxed for 30 minutes, followed by addition of 44.8g. of $ZrO(OAc)_2 \cdot H_2O$. Gas was evolved during this time and the mixture turned pea green. After 2 hours at reflux, 196.4g. of 85 percent $H_3PO_4$ was added. Reflux was continued for 3 additional hours during which time the color of the mixture became blue. The mixture was put into a tray in an oven to dry at 130°C. The resulting solid was ground to 60–200 mesh.

The catalyst (100 ml.) was charged to a fluid bed reactor at room temperature and 20 ml./min. of n-butane and 1000 ml./min. of air were passed through the catalyst. The reactor was heated at 450°C. for about 16 hours.

A mixture of 20 ml./min. of n-butane and 500 ml./min. of air was passed through the catalyst at 400°C. Maleic anhydride was determined by scrubbing the exit gases through water, followed by titration of an aliquot of the aqueous solution. In a one-hour sampling period, 68 percent MA yield was obtained at 62 percent selectivity.

EXAMPLE 2

A series of catalysts having P/V/Zr ratio (atomic) of 1/1.2/0.13 were prepared according to the procedure in Example 1, except that the amount of glycolic acid (GA) used was varied. These catalysts (100 ml.) were charged to a fluid bed and 20 ml./min. of n-butane and 1000 ml./min. of air were passed through the catalyst. The reactor was heated at 450°C. for 16 hours.

A mixture of n-butane and air (butane/air = 0.04) was passed through the catalyst at 400°C. and the yields of maleic anhydride were determined as in the previous example. These results are given in Table I.

TABLE I

| Moles GA/<br>Moles $V_2O_5$ | $CT^a$<br>(Sec) | MA,<br>Wt. % | MA<br>Selectivity | $A.I.^b$ |
| --- | --- | --- | --- | --- |
| 2.0 | 3.3 | 3 | 20 | 3.8 |
| 1.0 | 3.3 | 11 | 23 | 1.3 |
| 0.54 | 3.3 | 44 | 49 | 1.1 |
| 0.46 | 5.0 | 56 | 58 | 0.71 |
| 0.31 | 3.3 | 54 | 64 | 0.80 |

$^a$Contact Time
$^b$Attrition Index

EXAMPLE 3

A series of catalysts having different P/V/Zr ratios were prepared according to the procedure given in Example 1. These catalysts (100 ml.) were charged to a fluid bed reactor and 20 ml./min. of n-butane and 1,000 ml./min. of air were passed through the catalyst. The reactor was heated at 450°C. for 16 hours.

A mixture of n-butane and air (butane/air = 0.04) was passed through the catalysts at 400°C. and the yields of maleic anhydride were determined as in previous examples. The results are given in Table II. The data indicate that a zirconium level must be used that gives a balance of proper activity, selectivity, and physical stability.

TABLE II

| Atomic Ratio<br>P/V/Zr | $CT (Sec)^a$ | MA<br>Wt.% | Selectivity | $A.I.^b$ |
| --- | --- | --- | --- | --- |
| 1/1.2/0.13 | 3.3 | 56 | 58 | 0.71 |
| 1/1.2/0.093 | 5.0 | 47 | 64 | 1.10 |
| 1/1.2/0.058 | 5.0 | 47 | 72 | 1.20 |

$^a$Contact Time
$^b$Attrition Index

EXAMPLE 4

A catalyst having a $V/P/Zr/SiO_2$ ratio (atomic) of 1/1.2/0.09/0.35 was prepared as follows: 129g. of $V_2O_5$ and 30 ml. of 70 percent aqueous glycolic acid were added to 500 ml. of water. The mixture was refluxed for 30 minutes, followed by addition of 32g. of $ZrO(OAc)_2 \cdot H_2O$. During this time gas was evolved and the mixture turned pea green. After 2 hours at reflux, 196.4g. of 85 percent $H_3PO_4$ was added. Reflux was continued for 3 hours. The mixture turned blue. To the mixture 100 g. of 30 percent silica sol was added and reflux continued for 15 minutes. The mixture was put into an oven to dry at 130°C. The resulting solid was ground to 60–200 mesh.

The catalyst (100 ml.) was charged to a fluid bed reactor at room temperature and 20 ml./min. of n-butane and 1,000 ml./min. of air were passed through the catalyst. The reactor was heated at 450°C. for about 16 hours.

A mixture of 30 ml./min. of n-butane and 750 ml./min. of air was passed through the catalyst at 400°C. Maleic anhydride was determined by scrubbing the exit gases through water, followed by titration of an aliquot of the aqueous solution. In a 1-hour sampling period, 61 percent MA yield was obtained at 65 percent selectivity. The attrition index (A.I.) from the accelerated test was 0.7. This is superior to the A.I. of 1.1 for the same catalyst composition without $SiO_2$.

EXAMPLE 5

A catalyst having a V/P/Zr atomic ratio of 1/1.2/0.09 was prepared as follows: 129 g. of $V_2O_5$ and 300 ml. of 37 percent aqueous formaldehyde solution was brought to reflux and held for one hour. To this was added 31 g. of $ZrO(OAc)_2 \cdot H_2O$ and reflux continued for an hour, followed by addition of 200 ml. of water and 196g. 85 percent $H_3PO_4$. The total mixture was refluxed for an additional 2½ hours. The mixture was dried in an oven at 130°C. The resulting solid was ground to 60–200 mesh.

The catalyst (100 ml.) was charged to a fluid bed reactor at room temperature and 40 ml./min. of n-butane and 1000 ml./min. of air were passed through the catalyst. The reactor was heated at 450°C. for about 16 hours.

A mixture of 30 ml./min. of n-butane and 750 ml./min. of air was passed through the catalyst at 425°C. Maleic anhydride was determined by scrubbing the exit gases through water followed by titration of an aliquot of the aqueous solution. In a 1-hour sampling period, 63 percent MA was obtained at 61 percent selectivity.

EXAMPLE 6

A catalyst having a P/V/Zr atomic ratio of 1/1.2/0.13 was prepared and conditioned according to the procedure of Example 1 except that 0.33 mole of pyruvic acid was used instead of glycolic acid. A mixture of n-butane and air (butane/air = 0.04) was passed through the catalyst at 400°C. (3.4 sec. contact time) and yield of MA was determined as in Example 1. A 55 percent MA yield was obtained at 60 percent selectivity.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A method for preparing a vanadium-phosphorus-zirconium catalyst composite that consists essentially of:

a  forming an aqueous mixture of a vanadium compound selected from the group consisting of $V_2O_5$, $VOCl_3$, $VO(NO_3)_3$, $NH_4VO_3$, and $VF_5$ and a reactant selected from the group consisting of hydroxyalkanoic acids having 2-3 carbon atoms and oxoalkanoic acids having 2-3 carbon atoms in a ratio of said reactant to vanadium compound of between about 0.05 and about 1, refluxing said mixture for between about 0.5 hour and 5 hours;

b  adding a zirconium salt selected from the group consisting of $ZrOCl_2 \cdot 4H_2O$, $ZrOCl_2 \cdot 8H_2O$, $ZrO(OAc)_2 \cdot H_2O$, $ZrCl_4$, $Zr(OAc)_4$, $Na_2ZrCl_6$, and $ZrOBr_2 \cdot xH_2O$, in a Zr/V atomic ratio of between about 0.0025 and about 0.5, continuing refluxing for between about 0.5 hour and about 5 hours;

c  adding phosphoric acid or a compound hydrolyzable to phosphoric acid, in a P/V atomic ratio of between about 1.1/1 and about 1.5/1, continuing refluxing for between about 0.5 hour and about 5 hours to form a slurry; and d  drying said slurry.

2. The method of claim 1, wherein said reactant is glycolic acid.

3. The method of claim 1, wherein said zirconium salt is zirconyl acetate.

4. The method of claim 2, wherein said zirconium salt is zirconyl acetate.

5. The method of claim 1, wherein said reactant is pyruvic acid.

* * * * *